United States Patent
Provonchee

(10) Patent No.: US 12,208,249 B2
(45) Date of Patent: Jan. 28, 2025

(54) METHODS AND DEVICES FOR FRACTURING A HYDROGEL PRIOR TO DELIVERY THROUGH A NEEDLE

(71) Applicant: Advanced Aesthetic Technologies, Inc, Brookline, MA (US)

(72) Inventor: Richard Provonchee, Cushing, ME (US)

(73) Assignee: Advanced Aesthetic Technologies, Inc

( * ) Notice: Subject to any disclaimer, the term of this patent is extended or adjusted under 35 U.S.C. 154(b) by 1014 days.

(21) Appl. No.: 16/957,609

(22) PCT Filed: Jan. 4, 2019

(86) PCT No.: PCT/US2019/012334
§ 371 (c)(1),
(2) Date: Jun. 24, 2020

(87) PCT Pub. No.: WO2019/136238
PCT Pub. Date: Jul. 11, 2019

(65) Prior Publication Data
US 2020/0330695 A1    Oct. 22, 2020

Related U.S. Application Data

(60) Provisional application No. 62/632,559, filed on Feb. 20, 2018, provisional application No. 62/613,493, filed on Jan. 4, 2018.

(51) Int. Cl.
*A61M 5/315*    (2006.01)
*A61J 1/20*      (2006.01)
(Continued)

(52) U.S. Cl.
CPC ........ *A61M 5/31576* (2013.01); *A61J 1/2096* (2013.01); *A61M 5/19* (2013.01);
(Continued)

(58) Field of Classification Search
CPC ...... A61J 1/2086; A61J 1/2096; A61J 1/2089; A61M 5/19; A61M 5/2422; A61M 5/3145;
(Continued)

(56) References Cited

U.S. PATENT DOCUMENTS 3,482,597 A    12/1969  Smith, Jr.
3,527,712 A    9/1970   Renn et al.
(Continued)

FOREIGN PATENT DOCUMENTS

CN    103289107 B        2/2015
WO    WO-9601085 A1  *  1/1996  ............ A61B 17/20

OTHER PUBLICATIONS

Supplementary European Search Report received in European Patent Application No. 19736133.0, Completed Aug. 18, 2021, Mail date Aug. 27, 2021, 7 pages.
(Continued)

*Primary Examiner* — Laura A Bouchelle
(74) *Attorney, Agent, or Firm* — WOMBLE BOND DICKINSON (US) LLP; Deborah M. Vernon; Ricardo Joseph

(57) ABSTRACT

Hydrogel fracturing devices are described herein that include a chamber with an inlet, outlet, and at least one fracturing structure which extends across the entire internal diameter of the chamber. The fracturing structure includes one or more apertures or screens. The fracturing device may be connected to a syringe and/or ampoule containing a
(Continued)

hydrogel formulation. The hydrogel formulation may then be fractured by forcing the formulation through the fracturing device.

14 Claims, 11 Drawing Sheets

(51) Int. Cl.
 *A61M 5/19* (2006.01)
 *A61M 5/24* (2006.01)
 *A61M 5/31* (2006.01)

(52) U.S. Cl.
 CPC ........ *A61M 5/2422* (2013.01); *A61M 5/3145* (2013.01); *A61M 2207/00* (2013.01)

(58) Field of Classification Search
 CPC .............. A61M 5/31576; A61M 5/345; A61M 2207/00
 See application file for complete search history.

(56) References Cited

U.S. PATENT DOCUMENTS

| | | | |
|---|---|---|---|
| 3,757,780 A * | 9/1973 | Ishikawa | A61M 5/3145 604/190 |
| 4,061,143 A * | 12/1977 | Ishikawa | A61M 5/3145 604/190 |
| 4,316,462 A | 2/1982 | Baker | |
| 4,453,927 A | 6/1984 | Sinko | |
| 4,751,921 A | 6/1988 | Park | |
| 2001/0037091 A1 * | 11/2001 | Wironen | A61F 2/4601 604/82 |
| 2009/0270814 A1 | 10/2009 | Masi et al. | |
| 2011/0021999 A1 * | 1/2011 | Kowalski, III | A61M 5/3145 604/190 |
| 2012/0016319 A1 | 1/2012 | Zino Gutierrez | |
| 2017/0368226 A1 | 12/2017 | Pilkington et al. | |

OTHER PUBLICATIONS

Office Action issued Dec. 17, 2021 in co-pending Chinese Application No. 201980001235.3.

* cited by examiner

METHODS AND DEVICES FOR FRACTURING A HYDROGEL PRIOR TO DELIVERY THROUGH A NEEDLE

CROSS-REFERENCE TO RELATED APPLICATIONS

This application claims priority from U.S. Provisional Application Ser. No. 62/613,493, filed Jan. 4, 2018 and U.S. Provisional Application Ser. No. 62/632,559, filed Feb. 20, 2018, the contents of which are incorporated by reference herein.

BACKGROUND

Hydrogels can be used for in-vivo applications, including filling and bulking, drug delivery, and scaffold generation. While various delivery techniques may be used, depending on circumstance, injection with a needle is a common technique for delivering hydrogels into a patient.

SUMMARY

It has been found that some applications benefit particularly when a hydrogel is delivered in a fractured or particulate form. There is also a need for devices and methods whereby a coherent hydrogel contained within a syringe can be simply, easily, and aseptically fractured and then dispensed through a needle or other bored device. Various devices for and methods of controllably fracturing a hydrogel prior to delivery are provided herein. The disclosed devices and methods may be used to administer any type of hydrogel or formulation containing a hydrogel to a mammalian patient (e.g., a human or animal). Additionally, the disclosed devices and methods may be used to deliver hydrogel to a patient for any purpose, including cosmetic, reconstructive, or therapeutic applications.

Hydrogel fracturing devices are described herein that include a chamber with an inlet, outlet, and at least one fracturing structure which extends across the entire internal diameter of the chamber. The fracturing structure includes one or more apertures or screens. The fracturing device may be connected to a syringe and/or ampoule containing a hydrogel formulation. In some embodiments, the outlet of the syringe barrel is attached to the inlet of the fracturing device and a needle is attached to the outlet of the fracturing device. After the fracturing device is attached to a syringe, the needle may be inserted into a patient and the plunger of the syringe may then be inserted into the syringe's barrel to force the hydrogel present in the barrel through the fracturing device and the needle, into the patient.

In select embodiments, the disclosed fracturing device includes an outer wall defining a chamber therein, an inlet in fluid connection with the chamber, an outlet in fluid connection with the chamber, and at least one fracturing structure extending across an internal diameter of the chamber. In some such embodiments, the chamber may have a substantially circular cross-section. In these and other embodiments, the at least one fracturing structure is a screen or a mesh. The screen or mesh may include openings having a diameter of less than 1,000 microns and, in some embodiments, less than 500 microns. The at least one fracturing structure may be solid across the internal diameter of the chamber with the exception of one or more apertures formed in the fracturing structure. In some such embodiments, the one or more apertures may have a diameter of less than 1,000 microns or, in some cases, less than 500 microns. In select embodiments, the fracturing structure includes at least three apertures. In various embodiments, the at least one fracturing structure is funnel-shaped with a tapered region having an opening formed therein that decreases in width from the inlet to the outlet. In some such embodiments, the opening may decrease in width at least 20% from the inlet to the outlet. In some embodiments, the at least one fracturing structure may be retained in a fixed position relative to the inlet and the outlet, while in other embodiments, the at least one fracturing structure is movable relative to the inlet and the outlet. At least two fracturing structures may be present in the chamber.

The subject disclosure also relates to embodiments in which the presently disclosed fracturing device is coupled to a syringe containing a hydrogel formulation. In some such embodiments, the syringe may be attached to the inlet of the fracturing device. In these and other embodiments, a needle may be coupled to the outlet of the fracturing device or, in other embodiments, a second syringe may be coupled to the outlet of the fracturing device. In select embodiments, the disclosed fracturing device may be coupled to an ampoule containing a hydrogel formulation. In some such embodiments, the ampoule may be attached to the inlet of the fracturing device. In these and other embodiments, a syringe may be coupled to the outlet of the fracturing device.

Methods of producing a device for fracturing a hydrogel are also disclosed herein. The disclosed methods may include, in some embodiments, preparing a hydrogel formulation, filling a vessel with the hydrogel formulation, and coupling the vessel to a fracturing device. In some embodiments, the fracturing device includes an outer wall defining a chamber therein, an inlet in fluid connection with the chamber, an outlet in fluid connection with the chamber, and at least one fracturing structure extending across an internal diameter of the chamber. In these and other embodiments, the methods further include sterilizing the hydrogel formulation either prior to filling into the vessel or while in the vessel. In some cases, the disclosed methods also include fracturing the hydrogel formulation by forcing the hydrogel formulation through the fracturing device. In these and other embodiments, the vessel may be a syringe or an ampoule. In select embodiments, the hydrogel formulation may include at least 1% agarose by weight.

BRIEF DESCRIPTION OF THE DRAWINGS

FIG. 5A shows an exploded view of the exemplary fracturing device and FIG. 5B shows a perspective view of the exemplary fracturing device shown in FIG. 5A.

DETAILED DESCRIPTION

Figure 1:
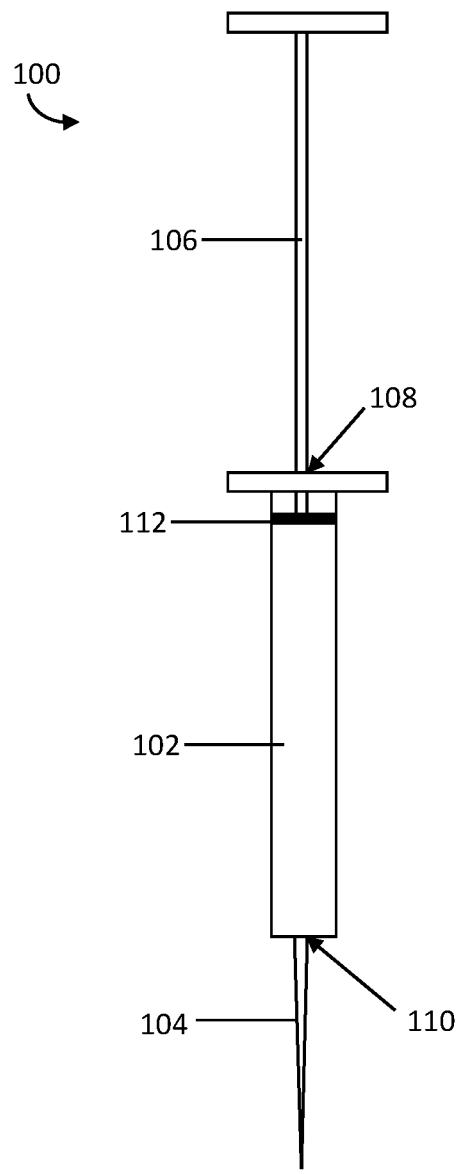
FIG. 1 shows a view of an exemplary syringe, in accordance with some embodiments of the subject disclosure.

As used herein, the term "hydrogel" refers to a hydrophilic network of polymer chains. Hydrogels are highly absorbent and, in some cases, are able to contain more than 90% water by weight. Any suitable type of hydrogel may be used in the disclosed methods. For example, in some embodiments, one or more biocompatible hydrogels may be used. Example hydrogels that may be used in the disclosed devices and methods include but are not limited to: agarose, methylcellulose, hyaluronan, silicone, polyacrylamides, polymacon, alginate, chitosan, collagen, and polyethylene oxide.

Hydrogels typically exist as large networks of polymer chains and can have relatively large molecular weights. As described herein in detail, the disclosed methods and devices may fracture a hydrogel (or hydrogel formulation) into at least two parts, thereby advantageously reducing the particle size of the hydrogel (or hydrogel formulation). A smaller particle size may allow the hydrogel to be administered through a smaller needle and/or be more precisely positioned.

Example hydrogel formulations that may be used in the disclosed devices and methods can vary depending on the type of application and patient needs. As used herein, the term "fractured hydrogel" refers to a hydrogel that has been divided into at least two parts. The term "fracturing" as used herein refers a process of dividing a hydrogel into at least two parts, which may include cutting, cleaving, or a combination thereof. As used herein, the term "formulation" or "hydrogel formulation" refers to any liquid or gel containing at least one hydrogel. In some embodiments, formulations comprising one or more hydrogels may be used. In particular embodiments, formulations including agarose (with or without other hydrogels present) may be used in connection with the disclosed methods and devices. In formulations that include agarose, the concentration of agarose may be at least 0.1%, 1%, 2%, 3%, 4%, 5%, or more by weight. The hydrogel(s) present in the formulation may be dispersed in an aqueous or non-aqueous medium, such as water or another fluid.

If desired, other compounds may also be included in the hydrogel formulations. For example, hyaluronic acid or a pharmaceutically acceptable salt thereof may be present in, for example, a weight percent of between 0.1 and 4%. In these and other embodiments, one or more enzymes, proteins, and/or amino acids may also be included in the formulations. In certain embodiments, enzymes to hydrolyze or break one or more bonds of the hydrogel or to liquify the hydrogel from a gelled state may be present. For example, in some embodiments, the enzyme hyaluronidase (Hylenex) may be included in the disclosed formulations. In these and other embodiments, the protein resilin (for example, in amounts between 0.01 and 0.1% by weight) may be included along with, in some cases, isoleucine, leucine, glycine, alanine, valine, lysine, and/or serine. Numerous configurations and variations will be apparent to those skilled in the art upon consideration of the subject disclosure. The disclosed methods and devices may be used in connection with any of the hydrogel formulations specifically mentioned herein or may be used in connection with any other type of hydrogel or hydrogel formulation.

Hydrogel formulations may take the form of a coherent monolithic gel that conforms to the shape of the containment at storage and use temperatures. Without fracturing, these hydrogel formulations may prove difficult or impossible to deliver through a needle. For example, some of these hydrogel formulations will form a coherent monolithic gel when loaded into a syringe and allowed to come to storage and/or use temperature or conditions. As described below in detail, the disclosed devices and methods are capable of fracturing a hydrogel to produce hydrogel particles of a size to be more easily delivered through a needle. In some cases, the size of the needle bore will determine the hydrogel particle size. In some embodiments, for example, when it is preferable to deliver the hydrogel formulation through a 30-gauge needle, the fracturing device will produce hydrogel particles with largest dimensions generally equal to or less than 160 m. In other embodiments, for example, when it is preferable to deliver the hydrogel formulation through a 10-gauge needle, the fracturing device will produce hydrogel particles with largest dimensions generally equal to or less than 2.69 mm. When the fractured hydrogel composition comprises particles that are soft and easily deformable, particle sizes somewhat larger than the bore of the delivery needle may be acceptable. Thus, the disclosed methods and devices can be used to deliver a hydrogel formulation through a desired needle bore by selecting an appropriate hydrogel particle size.

In some embodiments, when a hydrogel passes through the disclosed devices, the liquid content of the hydrogel formulation may be reduced as some liquid is expressed from the hydrogel formulation by the compressive forces imposed on it during the fracturing process. For example, in some cases, the liquid content of a hydrogel formulation may be reduced by at least 1%, at least 2%, at least 5%, or more after passing through the disclosed devices. This expressed liquid may provide a lubricating function to the hydrogel formulation as it is being fractured and when it is being delivered. Depending on the hydrogel formulation, this expressed liquid may be absorbed back into the hydrogel formulation after the fracturing process is complete. In some cases, liquid at the site of delivery may be absorbed into the hydrogel formulation during and/or after the hydrogel formulation delivery.

FIG. 1 illustrates an example syringe 100 having a barrel 102, a needle 104, and a plunger 106. Barrel 102 may store injectable formulations for a patient (e.g., hydrogel formulations), in some embodiments. As shown in FIG. 1, the barrel's inlet 108 is joined to plunger 106 and the barrel's outlet 110 is joined to needle 104. Any suitable configurations may be used to join plunger 106 and needle 104 to barrel 102. For example, plunger 106 may be formed to include a disc region 112 having approximately the same diameter as the inner diameter of barrel 102. In some such embodiments, when plunger 106 is forced into barrel 102, disc region 112 directly pushes on the contents of barrel 102 to force the contents out of the barrel's outlet 110. Needle 104 may be joined to barrel outlet 110 with any desired mechanism, such as a Luer fitting (sometimes referred to as a "Luer lock") although numerous other configurations are possible.

In some embodiments, syringe 100 may be loaded with a hydrogel formulation and attached to a fracturing device 200. The loaded syringe with attached fracturing device may then be sterilized, packaged, and sent to a medical provider in sterilized form. When ready for use, the pre-sterilized syringe with unfractured hydrogel formulation may be unpackaged, needle 104 attached to outlet 208 of fracturing device 200 and used by inserting needle 104 into a patient and pressing plunger 106 into barrel 102, thereby forcing the unfractured hydrogel formulation through fracturing device 200 and fracturing the hydrogel formulation, to dispense its contents into the patient.

In some embodiments, syringe 100 may be loaded with a hydrogel formulation and attached to a fracturing device 200. A second syringe may then be attached to outlet 208 of the fracturing device. The loaded syringe with attached fracturing device and second syringe may then be sterilized, packaged, and sent to a medical provider in sterilized form. When ready for use, the pre-sterilized syringe with unfractured hydrogel formulation, attached fracturing device and attached second syringe may be unpackaged and the hydrogel formulation may be passed between the syringes and through the fracturing device at least once. When fracturing is complete, the empty syringe and fracturing device may be removed and needle 104 may be attached to outlet 110 of syringe 100 and used by inserting needle 104 into a patient and pressing plunger 106 into barrel 102, thereby forcing the fractured hydrogel formulation into the patient.

In some embodiments, syringe 100 may be loaded with a hydrogel formulation and attached to a fracturing device 200. A second syringe may then be attached to outlet 208 of the fracturing device. The loaded syringe with attached fracturing device and second syringe may then be thermally sterilized, allowed to cool, and the hydrogel formulation can be passed through the fracturing device at least once. The sterilized and fractured hydrogel formulation may then be packaged and sent to a medical provider in sterilized and fractured form. When ready for use, the pre-sterilized syringe with pre-fractured hydrogel formulation may be unpackaged, the empty syringe and fracturing device removed, needle 104 attached and used by inserting needle 104 into a patient and pressing plunger 106 into barrel 102 to dispense its contents into the patient.

Figure 2:
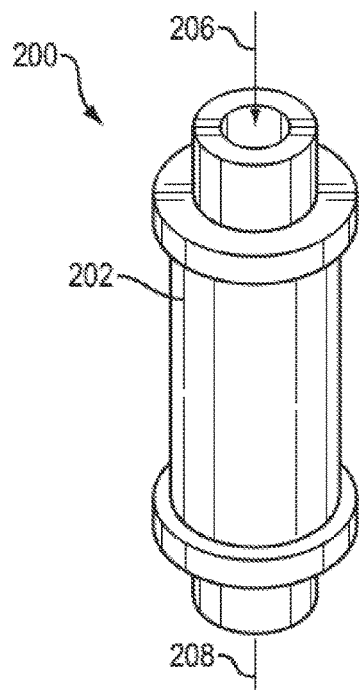
FIG. 2 shows a perspective view of an exemplary fracturing device, in accordance with some embodiments of the subject disclosure.

FIG. 2 is a perspective view of an example fracturing device 200. FIGS. 3A-3E are cut-away views of example fracturing devices 200a-200e, which are described below in detail. As shown in FIG. 2, fracturing device 200 includes an outer wall 202 defining a chamber 204 therein, which is clearly illustrated in FIGS. 3A-3E. Chamber 204 may have a substantially circular cross-section or may have a different shape, such as oval, square, or triangular. As shown in FIG. 2, fracturing device 200 has an inlet 206 and an outlet 208, each in fluid communication with chamber 204. In some embodiments, for example, passing the hydrogel formulation back and forth between two syringes and through the fracturing device may aid in fracturing the hydrogel formulation. In such embodiments, any given end of the fracturing device 200 may act as an inlet or an outlet, depending on the direction of flow at the time through the fracturing device.

In some embodiments, fracturing device 200 may include one or more fracturing structures designed to fracture a hydrogel passed through the chamber of the device. Example fracturing structures 210a-210e are shown in FIGS. 3A-3E. Fracturing structures (referred to generally herein as '210') may be fixed in a single position relative to inlet 206 and outlet 208 or, in some embodiments, may be axially moveable relative to inlet 206 and outlet 208. In some embodiments, a fracturing structure 210 extends the entire diameter of chamber 204 and includes one or more apertures or a screen. In particular, fracturing structure 210a shown in FIG. 3A includes one aperture positioned in approximately the center of fracture structure 210a. However, in some embodiments, a fracturing structure 210 may include a plurality of apertures, such as 2, 3, 4, 5, or more apertures. Fracturing structure 210b shown in FIG. 3B includes three apertures positioned approximately equidistantly from one another and between the center and outer edge of the fracturing structure 210b.

Figure 3A:
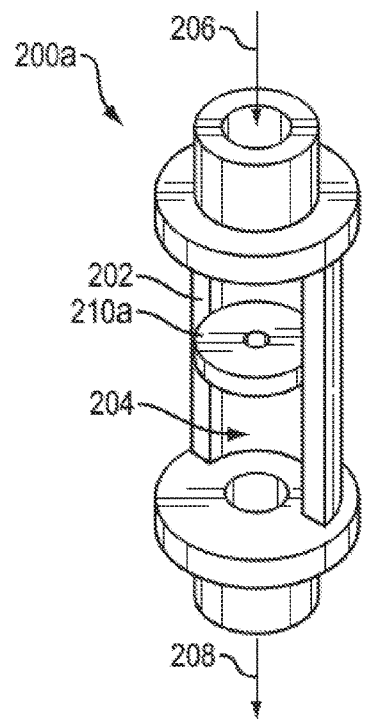
FIGS. 3A-3E show cut-away views of exemplary fracturing devices, in accordance with some embodiments of the subject disclosure.
Figure 3B:
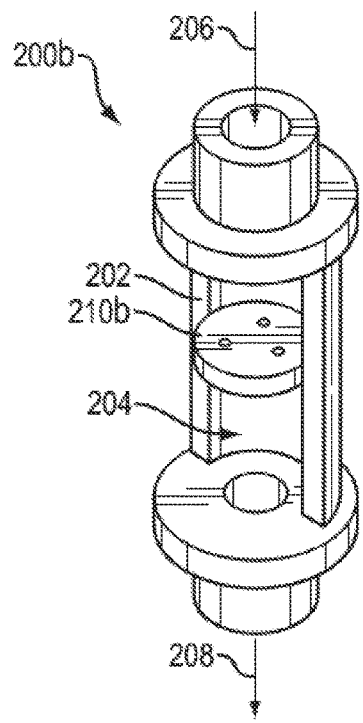
Figure 3C:
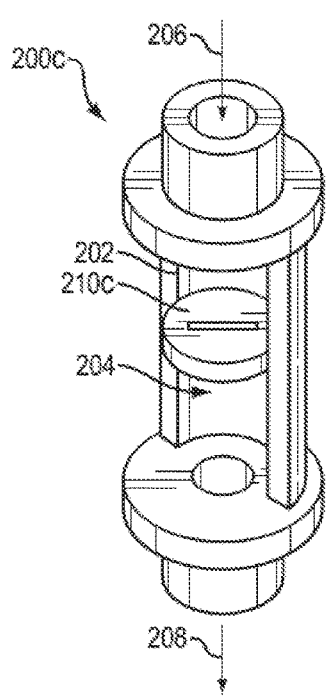
Figure 3D:
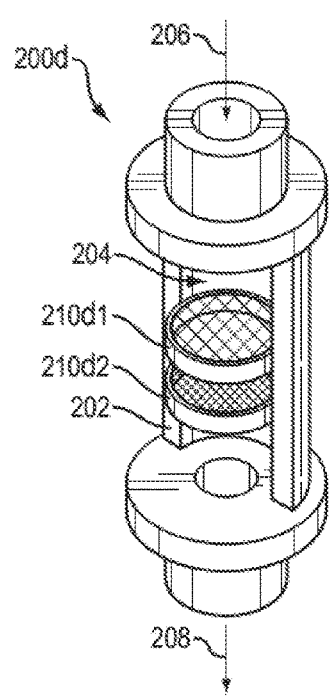

Apertures included in fracturing device 210 may have any desired dimensions and, in some cases, the dimensions of the aperture(s) may dictate the particle size of hydrogels passed through fracturing device 200. In some embodiments, fracturing structure 210 may have apertures with a diameter of less than 1000 microns, less than 500 microns, less than 250 microns, less than 125 microns, or less than 75 microns. As shown in FIG. 3C, fracturing structure 210c may include a slot-shaped aperture. Other aperture shapes are also contemplated, such as star-shaped, oval, square, or triangular-shaped.

In some embodiments, fracturing structure 210 includes one or more screens. In some such embodiments, the screen may have openings of any desired dimension. For example, a screen having openings less than 1000 microns, less than 500 microns, less than 250 microns, less than 125 microns, or less than 75 microns may be used, in some embodiments. Additionally, in some embodiments, two or more fracturing structures 210 may be positioned in a single chamber 204. For example, fracturing device 200d shown in FIG. 3D includes a first fracturing structure 210d1 and a second fracturing structure 210d2. Fracturing structures 210 may be positioned directly adjacent to one another or may be spaced apart from one another, as desired. In embodiments with more than one fracturing structure 210 included in chamber 204, the fracturing structures 210 may be positioned in order of decreasing aperture or screen opening size from inlet 206 to outlet 208. In some embodiments, two, three, four, five, or more fracturing structures 210 may be positioned inside chamber 204. Numerous configurations and variations are possible and contemplated.

Figure 3E:
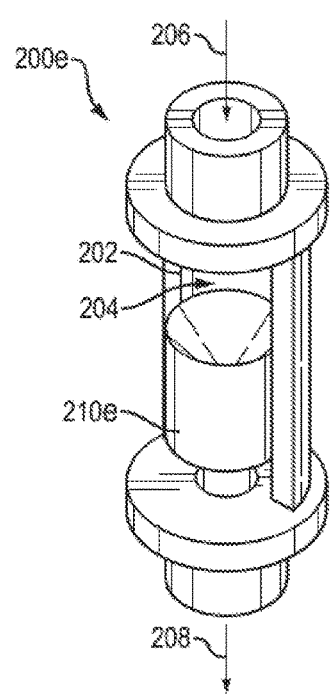

In some embodiments, fracturing structure 210 may be funnel-shaped, as shown in FIG. 3E. In particular, fracturing structure 210e shown in FIG. 3E includes a tapered region with an opening width that decreases from inlet 206 to outlet 208. The tapered region may have an opening width that decreases at least 10%, 20%, 50%, or more, in some embodiments. In embodiments with a fracturing structure 210 having one or more apertures, the apertures may also be tapered such that the aperture decreases in width from inlet 206 to outlet 208.

Fracturing devices 200a-200e are shown with significant void or dead volume for illustrative purposes. In some embodiments, it may be preferable to minimize this void or dead volume. In other embodiments, for example, when a second material is to be added to the hydrogel formulation and that second material is to be contained inside the fracturing device 200, a void or space is provided in or adjacent to the flow path of the fracturing device to contain the second material.

Fracturing device 200 may be constructed of any appropriate material, including but not limited to materials equipped for thermal sterilization. In some embodiments, fracturing device may be constructed of stainless steel or an alloy thereof. Additionally, in some embodiments, the components of fracturing device 200 (e.g., fracturing structure(s) 210, outer wall 202, inlet 206, and outlet 208) may be integrally formed from a single monolithic material or may be constructed from separate pieces and joined together (for example, by welding).

Figure 4:
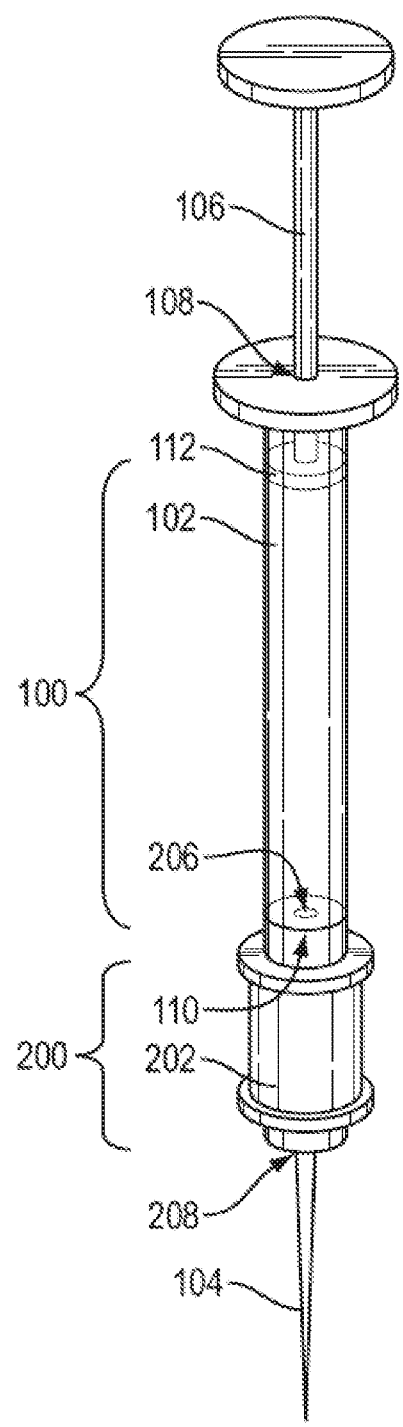
FIG. 4 is a perspective view of an exemplary fracturing device coupled to a syringe and a needle, in accordance with some embodiments of the subject disclosure.

In some embodiments, one or more fracturing devices 200 as described herein may be connected to a syringe 100. For example, in some embodiments, inlet 206 of a fracturing device 200 may be attached to the outlet 110 of a syringe 100 containing a hydrogel formulation in its barrel 102. FIG. 4 shows such a configuration. Any suitable attachment mechanism may be used to connect fracturing device 200 to syringe 100, such as, for example, a Luer fitting. A hydrogel formulation may then be forced through the barrel 102 of the syringe 100, into the chamber 204 of the fracturing device 200 and through the outlet 208 of the fracturing device. Depending on the hydrogel formulation and the desired application, only one pass through the fracturing device 200 may be needed. In some such embodiments, needle 104 may be attached to outlet 208 of the fracturing device 200. Note that the dimensions of syringe 100 and fracturing device 200 are not necessarily drawn to scale in FIG. 4. Moreover, chamber 204 of fracturing device 200 and/or barrel 102 of syringe 100 may have any suitable dimension, including a length of between 5 millimeters and 100 millimeters and/or a diameter of between 5 millimeters and 50 millimeters.

In cases when more than one pass through the fracturing device 200 is needed to obtain the desired hydrogel particle size, it may prove advantageous to attach an empty syringe to outlet 208 of fracturing device 200 and pass the hydrogel formulation back and forth between the syringes and through the fracturing device 200 a number of times, thereby further fracturing the hydrogel. In some embodiments, multiple passes through a fracturing device 200, regardless of the structure of that fracturing device 200, may further reduce the particle size from the size expected from one pass through that fracturing device 200.

If it is desired to mix another material with the hydrogel formulation during the fracturing procedure, the other material may be contained in a second syringe that is attached to the outlet 208 of the fracturing device 200. In some such embodiments, passing the hydrogel between the two syringes and through the fracturing device may fracture the hydrogel and also mix the other material with the fractured hydrogel. In other embodiments in which a second material is to be added to the hydrogel formulation, the second material may be contained inside the fracturing device 200 and may be mixed with the hydrogel formulation as it passes from the syringe 100 through the fracturing device 200. In some embodiments, two or more fracturing devices 200 may be joined together in sequence and coupled to a syringe 100. Depending on desired functionality, inlet 206 and outlet 208 of fracturing device 200 may be outfitted with the appropriate Luer fitting to interface and connect with adjoining device(s). Accordingly, in some embodiments, inlet 206 and outlet 208 of fracturing device 200 may include either a female or a male Luer fitting. Numerous configurations are possible and contemplated by the subject disclosure.

In some embodiments, a needle 104 may be attached to the outlet 208 of the fracturing device 200, as shown in FIG. 4. As used herein, the term "needle" refers to any type of bored device, including blunt-tipped and sharp-tipped devices, rigid and non-rigid devices, cannulas, and other bored devices. Needle 104 may have any desired dimensions. For example, in some cases, needle 104 may have a gauge of less than 50, 40, 30, 20, 15, 10, or less. As will be understood, using a smaller needle for hydrogel formulation injection may minimize a patient's discomfort. Additionally, a smaller needle size may allow for a finer line of hydrogel formulation to be placed and/or increased placement precision.

Although in FIG. 4 fracturing device 200 is illustrated as separate and distinct from syringe 100, in some embodiments, a fracturing device may be integrated with a syringe. For example, in some embodiments, a fracturing structure 210 may be contained inside barrel 102 of a syringe. In some such embodiments, fracturing structure 210 may extend across the entire internal diameter of barrel 102 and may include one or more apertures or a screen. In some such embodiments, fracturing structure 210 may be positioned adjacent to outlet 110. In other embodiments, a fracturing structure 210 may be positioned within outlet 110 and may extend across the diameter of outlet 110. In some particular embodiments, a fracturing structure 210 may be molded into the outlet 110 of a syringe. In other embodiments, a fracturing structure 210 may be included in a cannula affixed to a syringe. In some cases, a syringe with an integral fracturing device (i.e., a fracturing structure 210) may be permanently affixed to or non-removeable from the syringe. As will be understood, a syringe having an integral fracturing device may allow for a hydrogel to be fractured at any desired time, such as during manufacture or at the point of care.

Figure 5A:
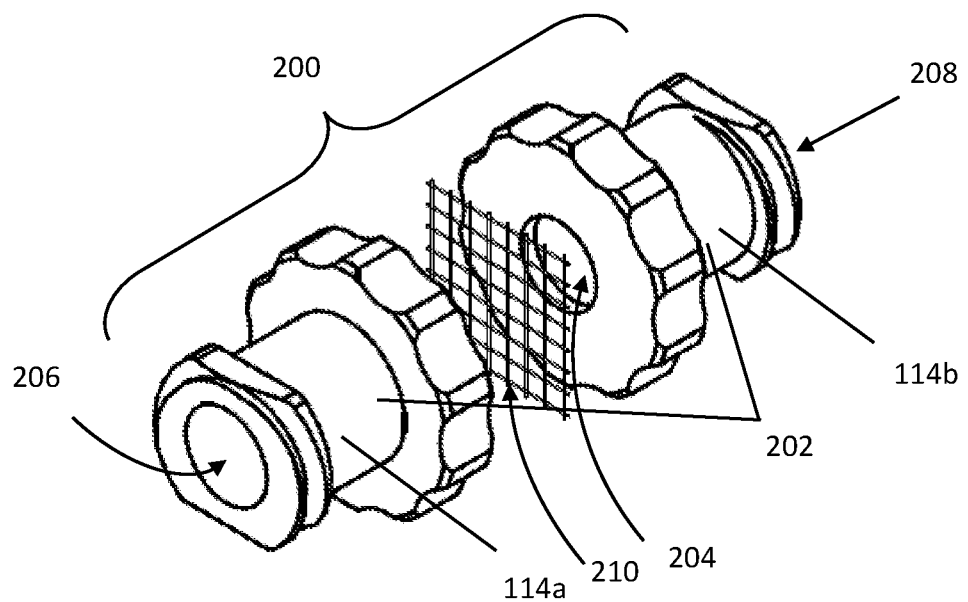
FIGS. 5A-5B show an exemplary fracturing device, in accordance with some embodiments of the subject disclosure. In particular.
Figure 5B:
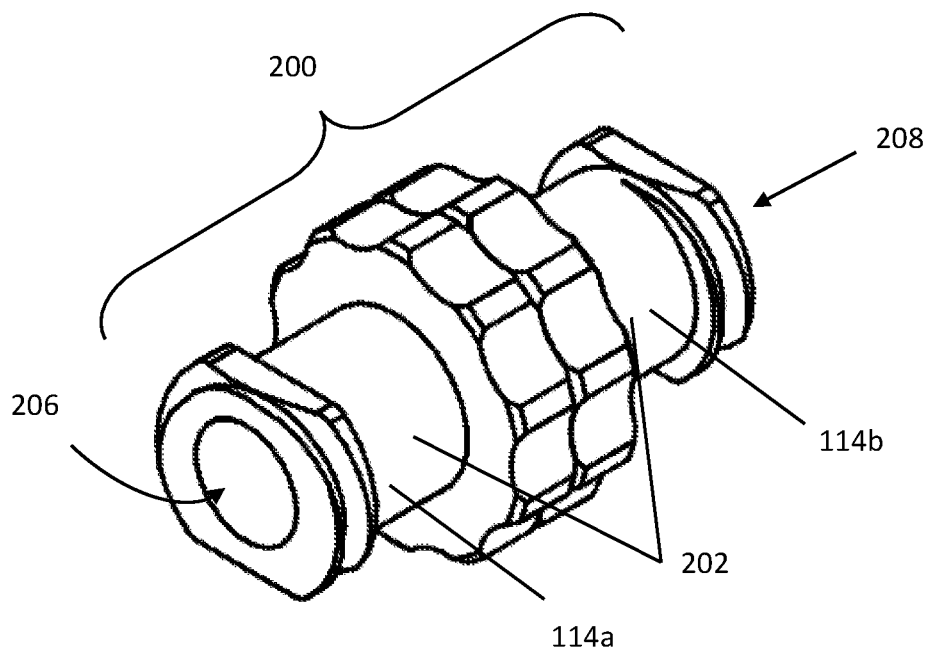

In select embodiments, a fracturing device 200 may be formed of two Luer fittings joined together with a fracturing structure 210 positioned therebetween. FIGS. 5A and 5B show such an example fracturing device 200. Specifically, FIG. 5A shows an exploded view of exemplary fracturing device 200 and FIG. 5B shows a perspective view of the exemplary fracturing device 200 shown in FIG. 5A. As shown in FIGS. 5A and 5B, the fracturing device 200 includes an inlet 206 formed by a first Luer fitting 114*a* and an outlet 208 formed by a second Luer fitting 114*b*. The walls of the Luer fittings 114*a*, 144*b* form the outer wall 202 and a chamber 204 is formed inside outer wall 202. A fracturing structure 210 may be positioned between inlet 206 and outlet 208, as shown in FIG. 5A. Fracturing structure 210 may be a screen or mesh, in some embodiments. The Luer fittings 114*a*, 114*b* may be bonded together (e.g., with adhesive, solvent, via ultrasonic welding, or by other suitable techniques. However, in other embodiments, the fracturing device 200 shown in FIGS. 5A and 5B may be formed as a single piece via injection molding around the fracturing device 210. Numerous configurations and variations are possible and contemplated herein.

In some example embodiments, a kit is provided with one or more syringes (with or without hydrogel contained therein), one or more fracturing devices, and/or one or more needles. In some embodiments, two or more fracturing devices having different aperture sizes and/or screen opening sizes are included in the kit. In some such embodiments, a user may select a fracturing device having the desired aperture size and/or screen opening size and join the selected fracturing device to the syringe and needle to be used. In these and other embodiments, one or more fracturing devices containing additive may also be included in the kit. In some such embodiments, a syringe may be coupled to a fracturing device containing selected additive(s). In some embodiments, the syringe may be provided in the kit coupled to or separate from a fracturing device included with the kit.

Figure 6:
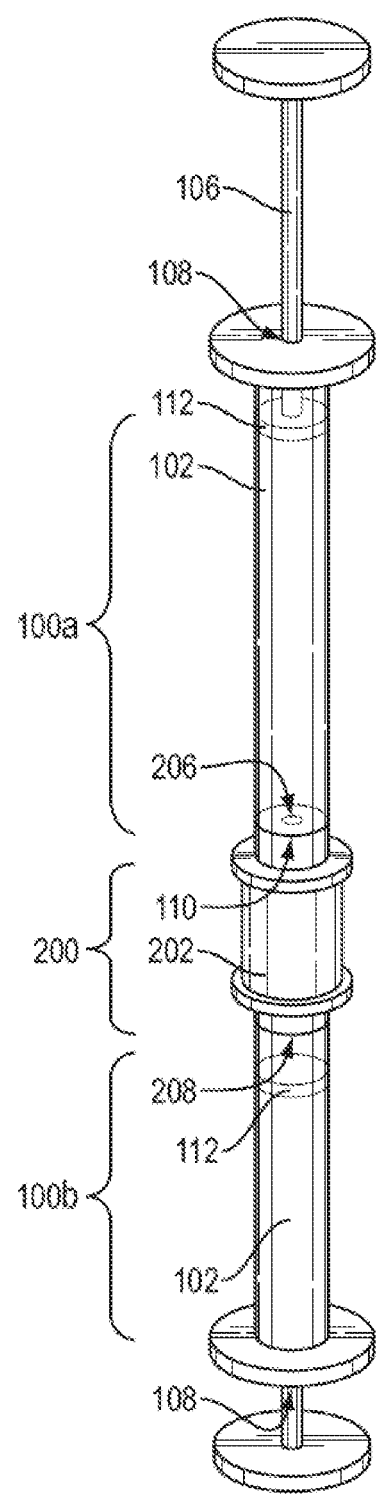
FIG. 6 is a perspective view of an exemplary fracturing device coupled to two syringes, in accordance with some embodiments of the subject disclosure.

FIG. 6 shows an example fracturing device 200 coupled to a first syringe 100a and a second syringe 100b, in accordance with some embodiments of the subject disclosure. In some embodiments, first syringe 100a may contain hydrogel and syringe 100b may be empty and the hydrogel can be passed between syringes 100a and 100b to fracture the hydrogel to a desired particle size. In some embodiments, inlet 206 of fracturing device 200 may be configured to engage outlet 110 of first syringe 100a and outlet 208 of fracturing device 200 may be configured to engage outlet 110 of second syringe 100b. Depending on the configuration of outlet 110 of first syringe 100a and outlet 110 of second syringe 100b, inlet 206 and outlet 208 of fracturing device 200 may both include female Luer fittings, may both include male Luer fittings, or may include one male and one female Luer fitting. As previously mentioned, passing or cycling a hydrogel between two attached syringes attached via a fracturing device 200 may allow the hydrogel to be fractured to a desired particle size and may also allow for complete homogeneous mixing of the hydrogel and any materials added to the hydrogel.

Figure 7A:
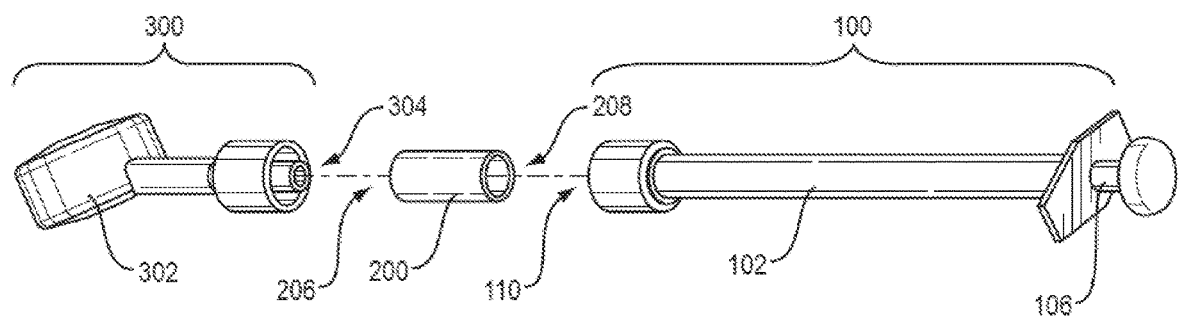
FIGS. 7A-7C are perspective views of an exemplary fracturing device coupled to a syringe and an ampoule, in accordance with some embodiments of the subject disclosure.
Figure 7B:
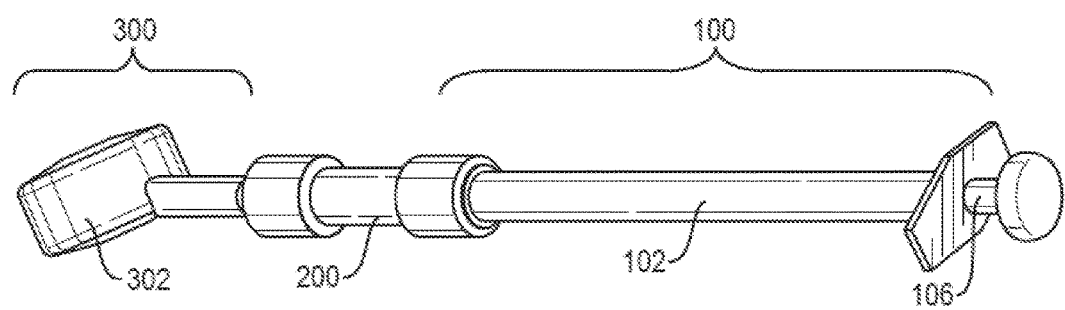
Figure 7C:
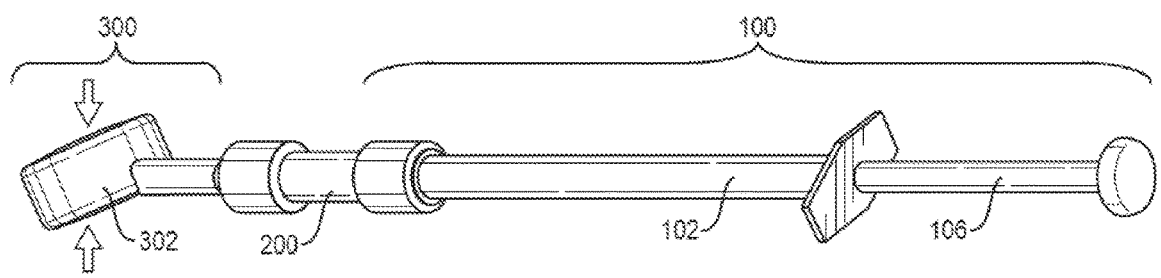

In some embodiments, a hydrogel is stored inside the barrel 102 of a syringe 100. However, in other embodiments, a hydrogel may be stored in an ampoule attached to or separate from a syringe 100. FIGS. 7A-7C illustrate an exemplary syringe 100 coupled to an ampoule 300 via a fracturing device 200. In particular, FIG. 7A is an exploded view of ampoule 300, fracturing device 200, and syringe 100. In some embodiments, ampoule 300 may be deformable upon the application of pressure, such as a squeezing pressure manually applied by a user. As shown in FIG. 7A, ampoule 300 includes a reservoir 302 and may be separated from outlet 304 with a barrier which, upon breakage, allows fluid communication between reservoir 302 and outlet 304. However, in other embodiments, no barrier is present between reservoir 302 and outlet 304. Reservoir 302 of ampoule 300 may be implemented with any deformable or semi-rigid material, such as a polymeric material. For example, in select embodiments, reservoir 302 may be implemented with polyethylene and/or polypropylene. In some embodiments, ampoule reservoir 302 may be transparent or opaque. In particular embodiments, outlet 304 and reservoir 302 may be molded as a single piece from the same polymeric material. Outlet 304 of ampoule 300 may be configured to engage with inlet 206 of fracturing device 200, for example, via a Luer fitting on another type of attachment mechanism.

FIG. 7B illustrates ampoule 300 attached to fracturing device 200, which is coupled to syringe 100. Prior to use, hydrogel may be stored in reservoir 302. As shown in FIG. 7B, plunger 106 of syringe 100 is fully inserted into barrel 102 of syringe 100, indicating that syringe barrel 102 is empty. When ready for use, pressure may be applied to ampoule reservoir 302 (illustrated in FIG. 7C with arrows), thereby forcing at least some of the contents of ampoule reservoir 302 through outlet 304 and fracturing device 200 and into syringe 100. As shown in FIG. 7C, plunger 106 of syringe 100 is at least partially removed from barrel 102, indicating that hydrogel has been moved from ampoule reservoir 302 through fracturing device 200 and into syringe barrel 102. In some embodiments, hydrogel may be cycled between ampoule 300 and syringe 100 to provide additional fracturing. In these and other embodiments, a needle 104 or other injection device may be coupled to outlet 110 of syringe (or to inlet 206 of fracturing device 200, if desired). Devices that include ampoule 300 may be sterilized according to any desired method. For example, in some embodiments, the device components may be sterilized separately or while coupled together. For example, in some embodiments, hydrogel may be inserted into ampoule reservoir 302 and the full ampoule 300 may then be coupled to fracturing device 200 and syringe 100. While assembled, the ampoule, fracturing device 200, and syringe 100 may be sterilized (by any process discussed herein or any other known technique). Numerous configurations and variations are possible and will be understood by those skilled in the art upon consideration of the present disclosure.

The disclosed devices may be sterilized prior to use according to any known technique suited to the materials and content of the devices. For example, the devices may be sterilized thermally (for example, using an autoclave) or with radiation-based techniques. In some embodiments, a hydrogel formulation is pre-loaded into the barrel 102 of a syringe 100 or ampoule 300 and subsequently sterilized, along with needle 104. Fracturing device 200 may also be sterilized (either while connected to syringe 100 or while separate from syringe 100). When ready for use, fracturing device 200 and syringe 100 may be unpackaged, assembled (if required), and utilized in conjunction with needle 104 to provide a hydrogel formulation fractured immediately prior to delivery into a patient through needle 104. After use, the disclosed devices may be disposed of or reused after being sterilized, depending on application and health considerations.

Figure 8:
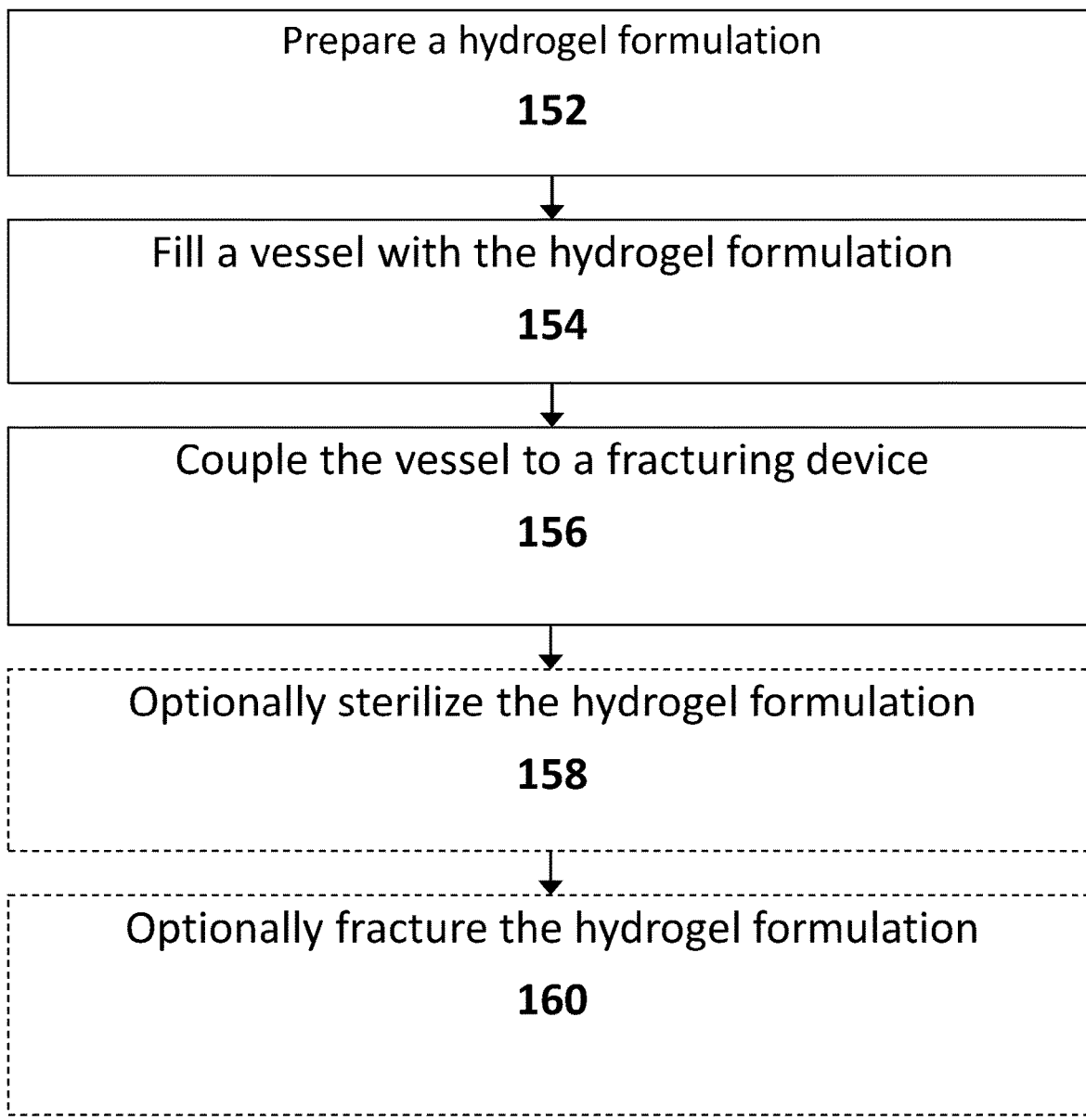
FIG. 8 is a flow diagram illustrating an exemplary method of producing a fracturing device, in accordance with embodiments of the subject disclosure.

FIG. 8 illustrates an exemplary method 150 of producing a fracturing device, in accordance with methods of the subject disclosure. As shown in FIG. 8, method 150 includes preparing a hydrogel formulation (Block 152). The hydrogel formulation may be prepared to have any desired specifications, including specifications of the hydrogel formulations previously described herein. For example, in some embodiments, a hydrogel formulation is prepared having at least 1% agarose by weight. Method 150 of FIG. 8 continues with filling a vessel with the hydrogel formulation (Block 154). The vessel filled with hydrogel formulation may be any suitable type of vessel, including a syringe or ampoule, as discussed herein with respect to various example embodiments. Method 150 continues with coupling the vessel to a fracturing device (Block 156). The fracturing device coupled to the vessel can be any type of fracturing device discussed herein. In some embodiments, the fracturing device includes an outer wall defining a chamber therein, an inlet in fluid connection with the chamber, an outlet in fluid connection with the chamber, and at least one fracturing structure extending across an internal diameter of the chamber.

As shown in FIG. 8, method 150 optionally includes sterilizing the hydrogel formulation (Block 158). In methods in which the hydrogel formulation is sterilized, sterilization can occur either prior to filling of the vessel or while the hydrogel formulation is in the vessel. Sterilization can be accomplished via any suitable technique, including by steam, autoclaving, and/or irradiation. Method 150 of FIG. 8 also optionally includes fracturing the hydrogel formulation (Block 160). The hydrogel formulation may, in some embodiments, be fractured by forcing the hydrogel formulation through the fracturing device.

Figure 9:
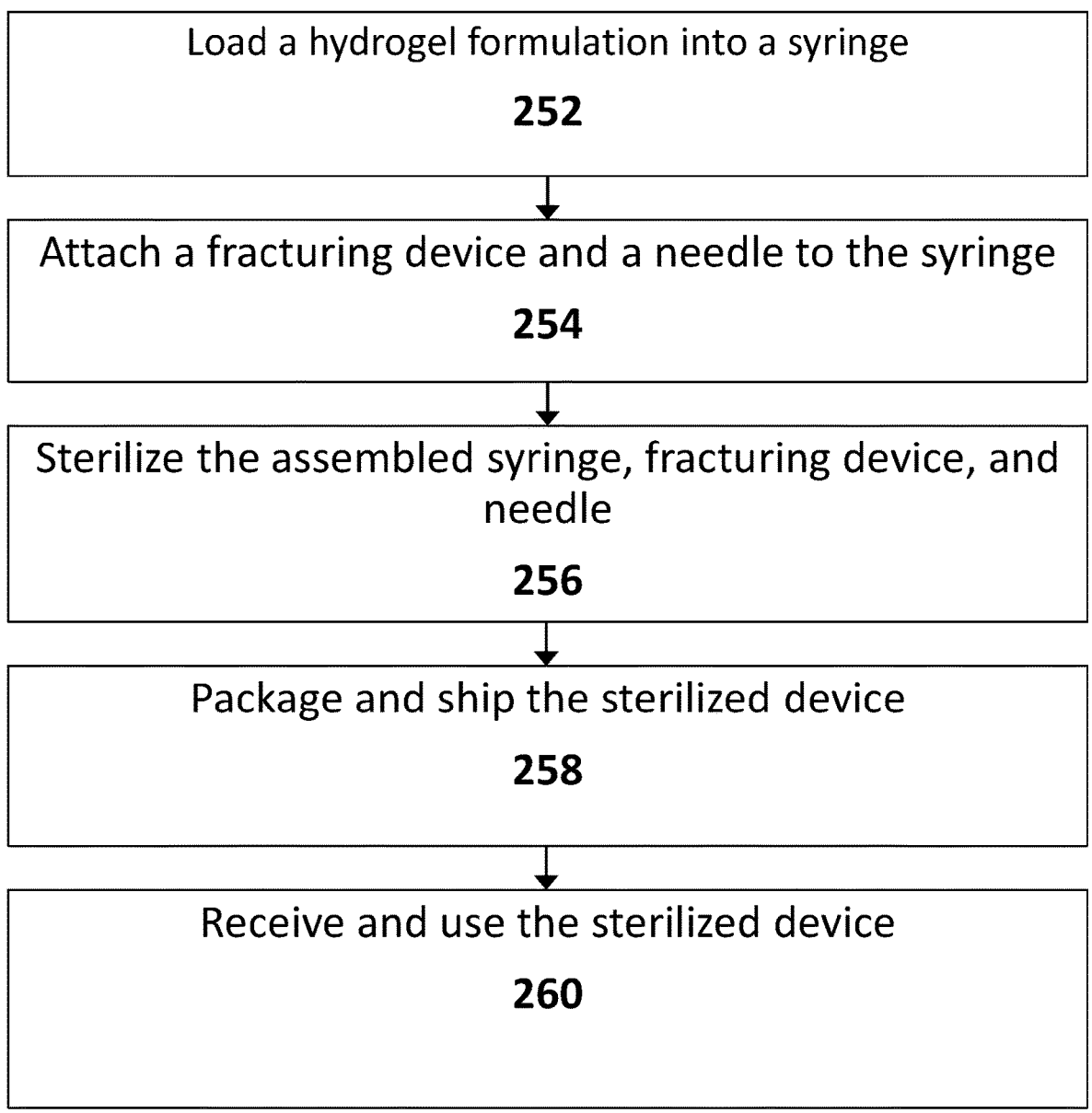
FIG. 9 is a flow diagram illustrating a single pass fracture process performed by a clinician, in accordance with some embodiments of the subject disclosure.

FIG. 9 illustrates an example method 250 in which a hydrogel is prepared for a single pass fracture by a clinician, in accordance with some example embodiments. As shown in FIG. 9, method 250 includes loading a hydrogel formulation into a syringe (Block 252). A fracturing device and a needle may then be attached to the syringe (Block 254). Thereafter, the syringe, fracturing device, and needle may sterilized, for example, with steam (Block 256). The sterilized device (assembled syringe, fracturing device, and needle) may then be packaged, stored, and/or shipped to a clinician site (Block 258). A clinician may then receive the sterilized device and use it on a patient (Block 260). Specifically, when ready for use, a clinician may unpackage the device and fracture the hydrogel immediately prior to dispensing the fractured hydrogel formulation into a patient.

Figure 10:
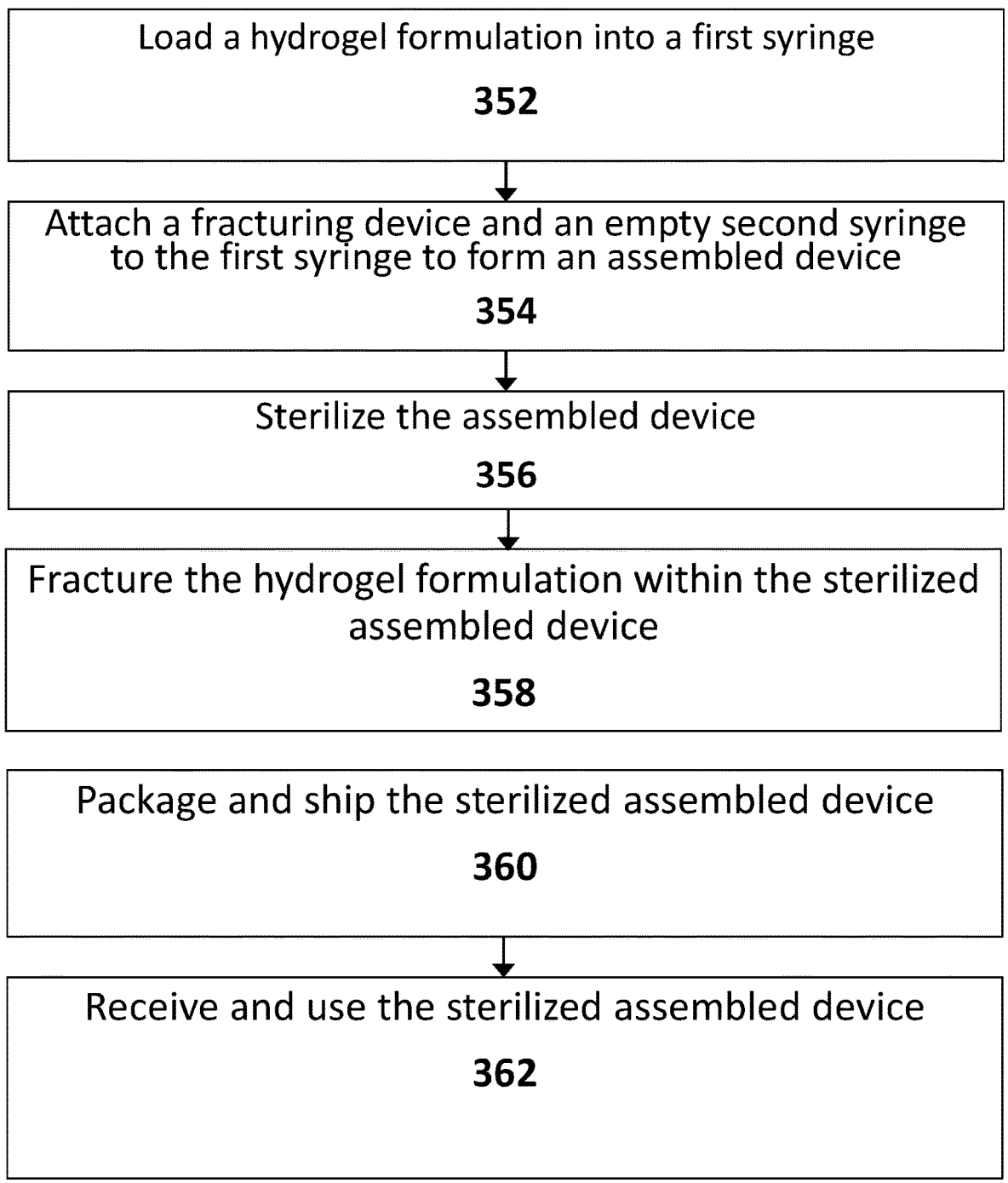
FIG. 10 is a flow diagram illustrating a single pass fracture process performed during production, in accordance with some embodiments of the subject disclosure.

FIG. 10 illustrates another example method 350 in which a hydrogel is prepared by a single pass fracture during production, in accordance with some example embodiments. As shown in FIG. 10, a hydrogel formulation may be prepared and loaded into a first syringe (Block 352). Thereafter, the first loaded syringe, fracturing device, and an empty second syringe may be assembled (Block 354) and sterilized, for example, with steam (Block 356). The sterilized hydrogel formulation may then be fractured (Block 358). In some embodiments, the sterilized hydrogel formulation is fractured by pushing the hydrogel formulation through from the loaded first syringe through the fracturing device and into the second syringe. The fractured hydrogel may then be packaged, stored, and/or shipped to a clinician site (Block 360). When ready for use, a clinician may unpackage the device (e.g., the fracturing device and the second syringe), attach a needle, and dispense the fractured hydrogel formulation into a patient (Block 362).

Figure 11:
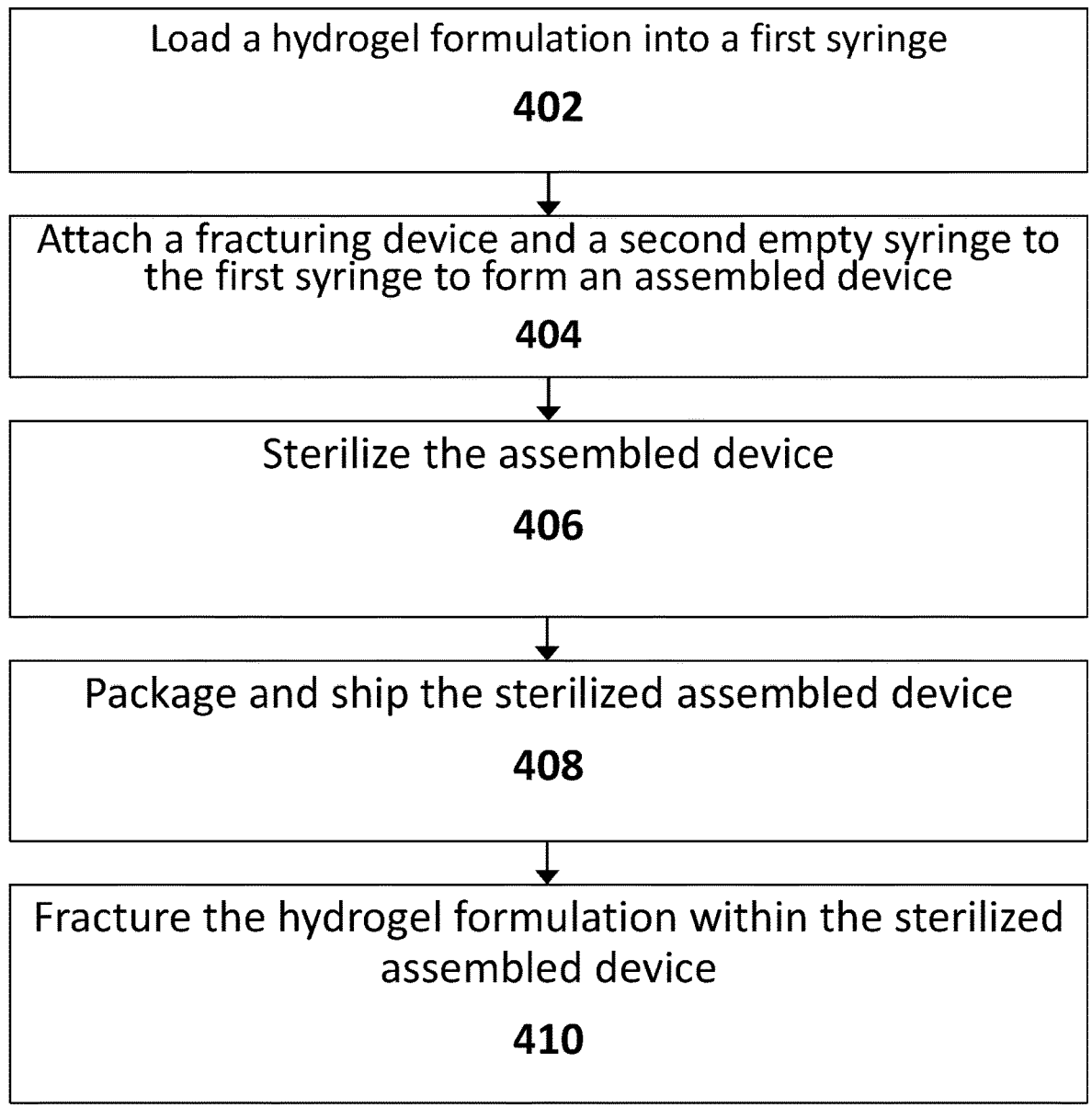
FIG. 11 is a flow diagram illustrating a multiple pass fracture and/or mixing process performed by a clinician, in accordance with some embodiments of the subject disclosure.

FIG. 11 illustrates an example method 400 in which a hydrogel is prepared by a multiple pass fracture and/or mixing process performed by a clinician, in accordance with some embodiments of the subject disclosure. As shown in FIG. 11, a hydrogel formulation may be prepared and loaded into a first syringe (Block 402). Thereafter, the loaded first syringe, fracturing device, and a second empty syringe may be assembled (Block 404) and sterilized, for example, with steam (Block 406). The sterilized device (first loaded syringe, fracturing device, and second empty syringe) may then be packaged, stored, and/or shipped to a clinician site (Block 408). When ready for use, a clinician may unpackage the device and fracture and/or mix the hydrogel (Block 410). In some embodiments, the hydrogel formulation is fractured by pushing the hydrogel from the first syringe through the fracturing device into the second syringe and then pushing the hydrogel from the second syringe through the fracturing device back into the first syringe. The hydrogel formulation may be passed through the fracturing device as many times as desired. Afterward, the clinician may attach a needle to the device and dispense the fractured hydrogel formulation into a patient.

Figure 12:
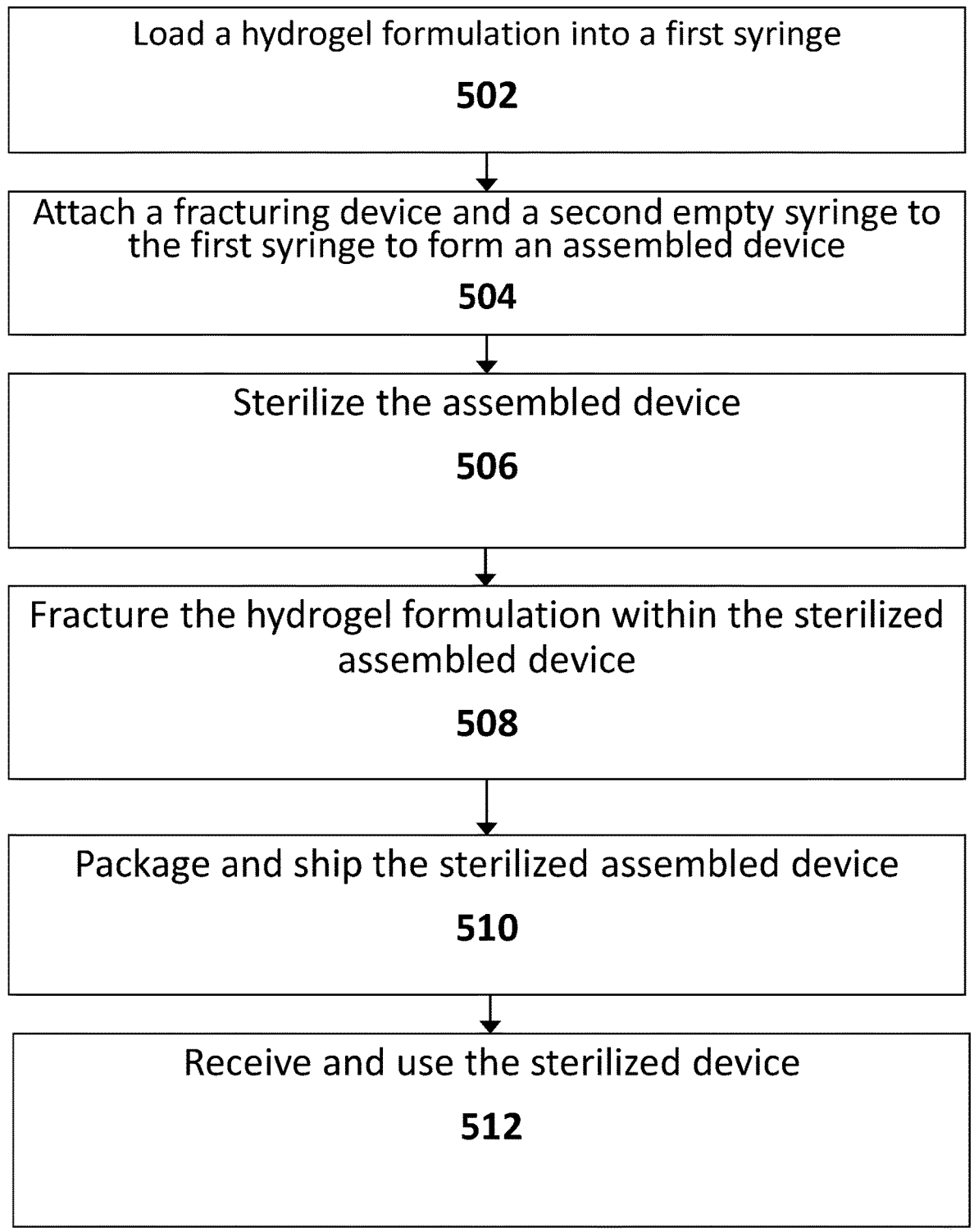
FIG. 12 is a flow diagram illustrating a multiple pass fracture and/or mixing process performed during production, in accordance with some embodiments of the subject disclosure.

FIG. 12 illustrates an example method 500 in which a hydrogel is prepared by a multiple pass fracture and/or mixing process performed during production, in accordance with some embodiments of the subject disclosure. As shown in FIG. 12, a hydrogel formulation may be prepared and loaded into a first syringe (Block 502). Thereafter, the first loaded syringe, fracturing device, and an empty second syringe may be assembled (Block 504) and sterilized, for example, with steam (Block 506). The sterilized assembled device (loaded first syringe, fracturing device, and empty second syringe) may then be fractured and/or mixed by pushing the hydrogel formulation from the loaded first syringe through the fracturing device and into the second syringe (Block 508). The hydrogel formulation may then be passed back from the second syringe through the fracturing device into the first syringe. The hydrogel formulation may be passed through the fracturing device as many times as desired. After fracturing and/or mixing, the fractured hydrogel may then be packaged, stored, and/or shipped to a clinician site (Block 510). When ready for use, a clinician may unpackage the device (the fracturing device and the second syringe), attach a needle, and dispense the fractured hydrogel formulation into a patient (Block 512).

The disclosed devices and methods can provide numerous benefits to users. For example, some hydrogel formulations undergo thermoreversible particle aggregation, meaning that even after being fractured to a smaller particle size, upon heating, the hydrogel particles congeal and revert back to the original particle size. Fracturing a hydrogel at the point of delivery is a new concept that the disclosed devices and methods are able to accomplish. Some previous hydrogel delivery techniques relied on radiation-based methods to preserve the small particle size of a hydrogel after a fracturing process. However, the disclosed devices and methods advantageously allow for thermal sterilization techniques to be utilized while also providing a small hydrogel particle size for delivery. Additionally, the disclosed devices allow a high level of control over the hydrogel particle size, permitting a particle size to be selected based on the application of the hydrogel. Furthermore, if a small hydrogel particle size is desired, a needle of minimal size can be used, resulting in less patient discomfort and healing time. Additionally, the disclosed devices can allow for convenient fracturing of a hydrogel formulation after sterilization and before final packaging while maintaining sterility, thereby reducing the requirement for any fracturing at the point of use. This may be accomplished by attaching a fracturing device to a syringe loaded with a hydrogel formulation and attaching a second syringe to the exit end of the fracturing device, thereby creating a closed system that can be sterilized, and allowing the hydrogel formulation to be fractured after sterilization without fear of contaminating the fractured hydrogel formulation. Final packaging can take place after the fracturing, in some cases. This may prove advantageous when the fracturing of the hydrogel formulation requires a technique that may be more easily accomplished in a manufacturing setting than at point of use. In addition to these benefits and advantages, the disclosed devices and methods may provide a hydrogel with a stable gel strength and a pH which remains relatively consistent over its shelf life.

The features and advantages described herein are not all-inclusive and, in particular, many additional features and advantages will be apparent to one of ordinary skill in the art in view of the present disclosure. Persons skilled in the relevant art can appreciate that many modifications and variations are possible in light of the above disclosure. What is claimed is:

What is claimed is:
1. A hydrogel fracturing device comprising:
an outer wall defining a chamber therein;
an inlet in fluid connection with the chamber;
an outlet in fluid connection with the chamber; and
at least one fracturing structure extending across an internal diameter of the chamber;
wherein the inlet of the fracturing device is attached to a syringe containing a hydrogel formulation, the outlet of the fracturing device is coupled to a needle, and the hydrogel comprises at least 1% agarose by weight.

2. The fracturing device of claim 1, wherein the chamber has a substantially circular cross-section.

3. The fracturing device of claim 1, wherein the at least one fracturing structure is a screen or a mesh.

4. The fracturing device of claim 3, wherein the screen or mesh includes openings having a diameter of less than 1,000 microns.

5. The fracturing device of claim 4, wherein the openings have a diameter of less than 500 microns.

6. The fracturing device of claim 1, wherein the at least one fracturing structure is solid across the internal diameter of the chamber with the exception of one or more apertures formed in the fracturing structure.

7. The fracturing device of claim 6, wherein the one or more apertures have a diameter of less than 1,000 microns.

8. The fracturing device of claim 7, wherein the one or more apertures have a diameter of less than 500 microns.

9. The fracturing device of claim 7, wherein the fracturing structure includes at least three apertures.

10. The fracturing device of claim 1, wherein the at least one fracturing structure is funnel-shaped with a tapered region having an opening formed therein that decreases in width from the inlet to the outlet.

11. The fracturing device of claim 10, wherein the opening decreases in width at least 20% from the inlet to the outlet.

12. The fracturing device of claim 1, wherein the at least one fracturing structure is in a fix position relative to the inlet and the outlet.

13. The fracturing device of claim 1, wherein the at least one fracturing structure is movable relative to the inlet and the outlet.

14. The fracturing device of claim 1, wherein at least two fracturing structures are present in the chamber.

* * * * *